US008324243B2

(12) United States Patent
Kraus et al.

(10) Patent No.: US 8,324,243 B2
(45) Date of Patent: Dec. 4, 2012

(54) DERIVATIVES OF THE AMINATED HYDROXYQUINOLINE CLASS FOR TREATING CANCERS

(75) Inventors: Jean-Louis Kraus, Marseille Cedex (FR); Olivier Blin, Marseilles (FR); Frederic Champavere, Paris (FR)

(73) Assignee: Biopharmed, Marseilles (FR)

(*) Notice: Subject to any disclaimer, the term of this patent is extended or adjusted under 35 U.S.C. 154(b) by 431 days.

(21) Appl. No.: 12/532,695

(22) PCT Filed: Mar. 25, 2008

(86) PCT No.: PCT/FR2008/000399
§ 371 (c)(1),
(2), (4) Date: Jan. 20, 2010

(87) PCT Pub. No.: WO2008/135671
PCT Pub. Date: Nov. 13, 2008

(65) Prior Publication Data
US 2010/0120856 A1 May 13, 2010

(30) Foreign Application Priority Data
Mar. 23, 2007 (FR) .................................... 07 02154

(51) Int. Cl.
A61K 31/04 (2006.01)
C07D 215/38 (2006.01)
(52) U.S. Cl. ........................................ 514/312; 546/159
(58) Field of Classification Search .................. 546/159; 514/312
See application file for complete search history.

(56) References Cited

FOREIGN PATENT DOCUMENTS
WO WO 00/74664 12/2000

OTHER PUBLICATIONS

Moret, Bioorg & med Chem Lett, vol. 16, 2006, 5988-5992.*
Oloff, Scott et al. "Application of Validated QSAR Models of D1 Dopaminergic Antagonist for Database Mining," *Journal of Medicinal Chemistry*, 2005, pp. 7322-7332, vol. 48, No. 23.
Database CA [Online] Accession No. 1999:446271, pp. 1-4, XP-002460959.
Gal, Shunit et al. "Novel multifunctional neuroprotective iron chelator-monoamine oxidase inhibitor drugs for neurodegenerative diseases. In vivo, selective brain monoamine oxidase inhibition and prevention of MPTP-induced striatal dopamine depletion," *Journal of Neurochemistry*, 2005, pp. 79-88, vol. 95, No. 1.
Warner, Victor D. et al. "Quantitative Structure-Activity Relationships for 5-Substituted 8-Hydroxyquinolines as Inhibitors of Dental Plaque," *Journal of Medicinal Chemistry*, 1977, pp. 93-96, vol. 20, No. 1.
Zheng, Hailin et al. "Design, synthesis, and evaluation of novel bifunctional iron-chelators as potential agents for neuroprotection in Alzheimer's, Parkinson's, and other neurodegenerative diseases," *Bioorganic & Medicinal Chemistry*, 2005, pp. 773-783, vol. 13, No. 3.
Database CA [Online] Accession No. 1973:147760, pp. 1-2, XP-002460960.
Moret, Vincent et al. "Synthesis and anti-HIV properties of new hydroxyquinoline-polyamine conjugates on cells infected by HIV-1 LAV and HIV-1 BaL viral strains," *Bioorganic & Medicinal Chemistry Letters*, 2006, pp. 5988-5992, vol. 16, No. 23.
Kolobielski, Marjan "The Synthesis of Substituted 8-Quinolinols," *Journal of Heterocyclic Chemistry*, 1968, pp. 275-277, vol. 101, No. 6.
Mishra, Amaresh et al. "Synthesis and characterisation of soluble aluminum complex dyes based on 5-substitued-8-hydroxyquinoline derivatives for OLED applications," *Dyes and Pigments*, 2005, pp. 89-97, vol. 66, No. 2.
Burckhalter, J. H. et al. "Amino and Cholormethylation of 8-Quinolinol. Mechanism of Preponderant *ortho* Substitution in Phenols under Mannich Conditions," *Journal of Organic Chemistry*, 1961, pp. 4078-4083, vol. 26.
Mishra, Amaresh et al. "Synthesis of 5-alkoxymethyl- and 5-aminomethyl-substituted 8-hydroxyquinoline derivatives and their luminescent Al(III) complexes for OLED applications," *Tetrahedron Letters*, 2004, pp. 6265-6268, vol. 45, No. 33.
Li, Xingwei et al. "Conducting poly-$N$-[5-(8-quinolinol)ylmethyl]aniline/nano-SiO$_2$ composite with fluorescence," *Materials Letters*, 2006, pp. 3342-3345, vol. 60, No. 28.
Database CA [Online] Accession No. 2006-136201, pp. 1-2, XP-002460961.
Database CA [Online] Accession No. 2004-818724, pp. 1-2, XP-002460962.
Database CA [Online] Accession No. 2005-1159137, pp. 1-2, XP-002460963.
Database CA [Online] Accession No. 1960-68227, pp. 1-4, XP-002460964.
Creech, H. J. et al. "Quantitative Studies of the Effects of Nitrogen Mustard Analogs and Other Alkylating Agents on Ascites Tumors in Mice," *Cancer Research*, Aug. 1, 1960, pp. 471-494, vol. 20, No. 7 (part 2).
Roth, Hermann et al. "Synthese und komplexierende Eigenschaften symmetrischer N,N'-Tetra-(8-hydroxychinolyl-5-methyl)-α,ω-diaminoalkine," *Arch. Pharm.*, 1982, pp. 131-135, vol. 315, No. 2.
Moret, Vincent et al. "Discovery of a new family of bis-8-hydroxyquinoline substitute benzylamines with pro-apoptotic activity in cancer cells: Synthesis structure—activity relationship, and action mechanism studies," *European Journal of Medicinal Chemistry*, 2009, pp. 558-567, vol. 44, No. 2.
Zheng, Hailin et al. "Novel multifunctional neuroprotective iron chelator-monoamine oxidase inhibitor drugs for neurodegenerative diseases: in vitro studies on antioxidant activity, prevention of lipid peroxide formation and monoamine oxidase inhibition," *Journal of Neurochemistry*, 2005, pp. 68-78, vol. 95, No. 1.
Written Opinion in International Application No. PCT/FR2008/000399, Apr. 8, 2009, pp. 1-21.

* cited by examiner

*Primary Examiner* — D M Seaman
(74) *Attorney, Agent, or Firm* — Saliwanchik, Lloyd & Eisenschenk

(57) ABSTRACT

The invention relates to compounds of the aminated hydroxyquinoline type capable of preventing the migration of metastases or tumoral cells. Such compounds are useful for treating cancers.

12 Claims, No Drawings

DERIVATIVES OF THE AMINATED HYDROXYQUINOLINE CLASS FOR TREATING CANCERS

CROSS-REFERENCE TO RELATED APPLICATION

This application is the U.S. national stage application of International Patent Application No. PCT/FR2008/000399, filed Mar. 25, 2008, the disclosure of which is hereby incorporated by reference in its entirety, including all figures, tables and amino acid or nucleic acid sequences.

The present invention relates to derivatives of the aminated hydroxyquinoline class for treating cancers.

A considerable arsenal of drugs used in oncology is available, alongside treatments such as radiotherapy, oncological surgery and vaccination tests, but it turns out in fact that standard chemotherapy occupies a predominant place in cancer treatment, despite certain drawbacks associated with the fact that it is not or is only sparingly specific to cancer cells.

Nevertheless, molecular innovation in the field of chemotherapy remains a priority in the fight against cancer, either by improving existing drugs, or by developing new molecules. Certain types of cancer are particularly feared because of their low probability of remission, in particular for patients suffering from glioblastoma or cancerous glial cells (15 to 20% survival at 6 months). Drugs commonly used clinically, for instance cyclophosphamide or methotrexate, have little or no effect on this type of cancer (Herrlinger et al., Journal of Neuro-oncology, 2005, 71, 295-299).

In the case of certain cancers, Temodal® appears to be an effective medicament for treating patients suffering from
- multiform glioblastoma (a type of aggressive cerebral tumor). Temodal® is used in the case of newly diagnosed patients: it is first combined with radiotherapy, and is then used alone;
- malignant gliomas (cerebral tumors), for instance multiform glioblastoma or anaplastic astrocytoma, when the tumor has recurred or has worsened after a standard treatment.

The efficacy of this medicament is based on its capacity to cross the blood-brain barrier. This barrier limits access to cerebral tissue via the combined action of renewal of the cerebrospinal fluid and of several selective active transport systems. Inhibition of these systems may increase the cerebral penetration of the corresponding substrates, which explains the occurrence of medicinal interactions with central manifestations; it may also improve the access of antibiotics, anticancer agents or psychotropic agents to the brain.

Starting from this observation, the Applicant sought, in a first stage, to develop a novel family of compounds having capacities for very efficiently treating tumors, such as prostate and bowel tumors, and in particular glioblastomas. Specifically, it is highly desirable to have available products that can be administered in the lowest possible doses but that have anticancer efficacy at least comparable to, or even better than, the products of the prior art, while at the same time limiting the cytotoxicity on healthy cells.

In the particular case of glioblastomas, the assessment of the capacity for treatment with such compounds consisted in evaluating their efficacy via the use of preliminary tests on glioblastoma cell lines on which the commonly-used active principles have virtually no effect. In the context of these tests, the human cell lines were transfected glioblastoma U87/GFP, which express the protein GFP (Green Fluorescent Protein). GFP is known as being a highly efficient fluorescence marker, which may be used in a live medium.

A first series of tests was based on tests of survival of treated cells, such as carcinoma cells (KB3). The tests consist in measuring the number of surviving cells after placing in contact with these compounds under suitable operating conditions. Reference tests are performed in the absence of such compounds.

A second series of tests consisted in determining the capacities of these compounds to inhibit the proliferation and migration of U87/GFP cells defined previously. Such an inhibition of migration and proliferation makes it possible to reduce, or even to prevent, the metastasis process, which is one of the most important factors in the development of many cancers in man.

From these preliminary results, the Applicant found, surprisingly, that this family of compounds can not only present the capacities listed above, but also act on other types of cancer and tumor cells. Such cells are especially carcinomas, adenocarcinomas, hepatocarcinomas, lymphoblastomas and also sarcomas, myelomas, melanomas and mesotheliomas.

Consequently, one of the aims targeted by the present invention was that of providing novel compounds for treating or preventing diseases associated with the proliferation or migration of metastases and with the survival of cells or, more generally, of tumor cells, while at the same time not affecting, or only very moderately affecting, healthy cells. They should thus be very advantageously effective for treating cancer cells mentioned above, while at the same time limiting the toxicity of these compounds.

The novel class of compounds of aminated hydroxyquinoline derivative type has the properties listed above.

The present invention thus relates to compounds of formula (I):

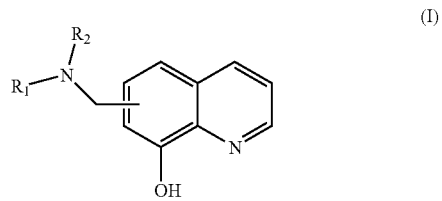

the group —$CH_2$—$NR_1R_2$ being in the ortho, meta or para position relative to the —OH group, in which:

one of the radicals $R_1$ and $R_2$ represents a hydrogen atom, a $C_1$ to $C_{10}$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 4, a $C_4$ to $C_6$ group —$(CH_2)_n$-heterocycloalkyl in which the heteroatom represents N, O or S, n being an integer between 0 and 4, or alkylphenyl in which the alkyl represents $C_1$ to $C_{10}$, the phenyl group being unsubstituted or substituted with 1 or 2 halogen atoms chosen from F, Br, I and Cl or with —$CF_3$;

or one of the radicals $R_1$ and $R_2$ represents a group of formula (II) linked to the asymmetric carbon

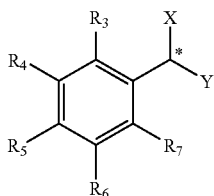

in which $R_3$, $R_4$, $R_5$, $R_6$ and $R_7$, independently of each other, represent a hydrogen atom, a $C_1$ to $C_{10}$ alkyl group, —$CF_3$, —$NO_2$, an N-5-methylene-8-hydroxyquinoline group, 1 or 2 halogen atoms chosen from F, Br, I and Cl or a group —O—R, R being a $C_1$ to $C_4$ alkyl group or —$CF_3$, X or Y represents a hydrogen atom, a $C_1$ to $C_{10}$ alkyl group, an aryl that is unsubstituted or substituted with a $C_1$ to $C_{10}$ alkyl group, —$CF_3$ or —$NO_2$, the other of the radicals $R_1$ and $R_2$ representing an H atom, a tert-butoxycarbonyl group (Boc), 5-methylene-8-hydroxyquinoline or —$(CH_2)_n$-phenyl, n being an integer between 1 and 5;

or, when one of the groups $R_1$ and $R_2$ is a group Y—N—Y' in which Y is chosen from the group formed by —$(CH_2)_n$—, n being an integer between 1 and 10, —$(CH_2)_m$-phenyl-$(CH_2)_p$—, the phenyl being unsubstituted or substituted with 1 or 2 halogen atoms chosen from F, Br and Cl or with a $C_1$ to $C_{10}$ alkyl group, m and p being, respectively, integers between 1 and 4, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 10, the naphthalene group being unsubstituted or substituted with one or more groups chosen from $C_1$ to $C_{10}$ alkyl groups, —$CF_3$ and —O—R in which R is a $C_1$ to $C_{10}$ alkyl group, the other is chosen from the group formed by a hydrogen atom, a 5-methylene-8-hydroxyquinoline group and a Boc group;

or $R_1$ and $R_2$ form a piperazine in which at least one of the carbon atoms of the ring is substituted with a $C_1$ to $C_6$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 10, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof, with the exclusion of 5-((benzylamino)methyl)quinolin-8-ol, and 5-((1,4,8,12-tetraazacyclopentadecan-8-yl)methyl)quinolin-8-ol, tri-tert-butyl 12-((8-hydroxyquinolin-5-yl)methyl)-1,4,8,12-tetraazacyclopentadecane-1,4,8-tricarboxylate, tri-tert-butyl 11-((8-hydroxyquinolin-5-yl)methyl)-1,4,8,11-tetraazacyclotetradecane-1,4,8-tricarboxylate, 5-((1,4,8,11-tetraazacyclotetradecan-1-yl)methyl)quinolin-8-ol, tri-tert-butyl 11-(3-((4,11-bis(tert-butoxycarbonyl)-8-((8-hydroxyquinolin-5-yl)methyl)-1,4,8,11-tetraazacyclotetradecan-1-yl)methyl)benzyl)-1,4,8,11-tetraazacyclotetradecane-1,4,8-tricarboxylate, 5,5'-(propane-1,3-diylbis(azanediyl))bis(methylene) diquinolin-8-ol, 5-((8-(4-((1,4,8,11-tetraazacyclotetradecan-1-yl)methyl) benzyl)-1,4,8,11-tetraazacyclotetradecan-1-ylmethyl) quinolin-8-ol, di-tert-butyl 4,8-bis((8-hydroxyquinolin-5-yl)methyl)-1,4,8,11-tetraazacyclotetradecane-1,1'-dicarboxylate, 5,5'-(1,4,8,11-tetraazacyclotetradecane-1,1'-diyl)bis(methylene)diquinolin-8-ol, 5,5'-(1,4-phenylenebis(methylene))bis(azanediyl)bis(methylene)diquinolin-8-ol, 5-(((8-hydroxyquinolin-5-yl)(4-methylbenzyl)amino)methyl)quinolin-8-ol, tert-butyl 8-hydroxyquinolin-5-yl(4-methylbenzyl)carbamate, 5-((4-methylbenzylamino)methyl)quinolin-8-ol, 5-(naphthalen-1-ylmethylamino)quinolin-8-ol, 5,5'-(naphthalen-1-ylmethylazanediyl)diquinolin-8-ol, tert-butyl 8-hydroxyquinolin-5-yl(naphthalen-1-ylmethyl)carbamate, and 5-(((8-hydroxyquinolin-5-yl)(4-(trifluoromethyl)benzyl) amino)methyl)quinolin-8-ol.

According to one embodiment of the invention, preferred compounds are those of formula (I) in which:

one of the radicals $R_1$ and $R_2$ represents a hydrogen atom, a $C_1$ to $C_6$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 4, a $C_4$ to $C_6$ group —$(CH_2)_n$-heterocycloalkyl in which the heteroatom represents N, O or S, n being an integer between 0 and 4, or alkylphenyl in which the alkyl represents $C_1$ to $C_6$, the phenyl group being unsubstituted or substituted with 1 or 2 halogen atoms chosen from F, Br, I and Cl or with —$CF_3$;

or one of the radicals $R_1$ and $R_2$ represents a group of formula (II) linked to the asymmetric carbon

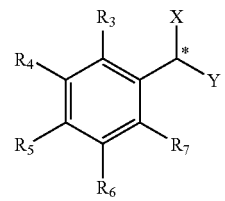

in which $R_3$, $R_4$, $R_5$, $R_6$ and $R_7$, independently of each other, represent a hydrogen atom, a $C_1$ to $C_6$ alkyl group, —$CF_3$, —$NO_2$, an N-5-methylene-8-hydroxyquinoline group, 1 or 2 halogen atoms chosen from F, Br, I and Cl or a group —O—R, R being a $C_1$ to $C_3$ alkyl group or —$CF_3$, X or Y represents a hydrogen atom, a $C_1$ to $C_6$ alkyl group, an aryl that is unsubstituted or substituted with a $C_1$ to $C_6$ alkyl group, —$CF_3$ or —$NO_2$, the other of the radicals $R_1$ and $R_2$ representing an H atom, a Boc group, 5-methylene-8-hydroxyquinoline or —$(CH_2)_n$-phenyl, n being an integer between 1 and 5;

or, when one of the groups $R_1$ and $R_2$ is a group Y—N—Y' in which Y is chosen from the group formed by —$(CH_2)_n$—, n being an integer between 1 and 6, —$(CH_2)_m$-phenyl-$(CH_2)_p$—, the phenyl being unsubstituted or substituted with 1 or 2 halogen atoms chosen from F, Br and Cl or with a $C_1$ to $C_6$ alkyl group, m and p being, respectively, integers between 1 and 4, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 6, the naphthalene group being unsubstituted or substituted with one or more groups chosen from $C_1$ to $C_6$ alkyl groups, —$CF_3$ and —O—R in which R is a $C_1$ to $C_6$ alkyl group, the other is chosen from the group formed by a hydrogen atom, a 5-methylene-8-hydroxyquinoline group and a Boc group;

or $R_1$ and $R_2$ form a piperazine in which at least one of the carbon atoms of the ring is substituted with a $C_1$ to $C_4$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 6, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof, besides the compounds excluded hereinabove.

Most preferably, the compounds of formula (I) are those in which:

one of the radicals $R_1$ and $R_2$ represents a hydrogen atom, a $C_1$ to $C_4$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 3, a $C_4$ to $C_6$ group —$(CH_2)_n$-heterocycloalkyl in which the heteroatom represents N, O or S, n being an integer between 0 and 3, or alkylphenyl in which the alkyl represents $C_1$ to $C_4$, the phenyl group being unsubstituted or substituted with 1 or 2 halogen atoms chosen from F and I or with —$CF_3$;

or one of the radicals $R_1$ and $R_2$ represents a group of formula (II) linked to the asymmetric carbon

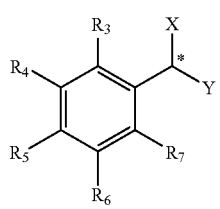

in which one of the radicals $R_3$, $R_4$, $R_5$, $R_6$ and $R_7$ represents an N-5-methylene-8-hydroxyquinoline group and the others represent a hydrogen atom, X or Y represents a hydrogen atom, a $C_1$ to $C_4$ alkyl group, an aryl that is unsubstituted or substituted with a $C_1$ to $C_4$ alkyl group, —$CF_3$ or —$NO_2$, the other of the radicals $R_1$ and $R_2$ representing H, a tert-butoxycarbonyl (Boc) group or 5-methylene-8-hydroxyquinoline;

or, when one of the groups $R_1$ and $R_2$ is a group Y—N—Y' in which Y is chosen from the group formed by —$(CH_2)_n$—, n being an integer between 1 and 4, —$(CH_{12})_m$-phenyl-$(CH_2)_p$—, the phenyl being unsubstituted or substituted with 1 or 2 halogen atoms chosen from F, Br and Cl or with a $C_1$ to $C_4$ alkyl group, m and p being, respectively, integers between 1 and 3, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 4, the naphthalene group being unsubstituted or substituted with one or more groups chosen from $C_1$ to $C_4$ alkyl groups, —$CF_3$ and —O—R in which R is a $C_1$ to $C_4$ alkyl group, the other is chosen from the group formed by a hydrogen atom, a 5-methylene-8-hydroxyquinoline group and a Boc group;

or $R_1$ and $R_2$ form a piperazine in which at least one of the carbon atoms of the ring is substituted with a $C_1$ to $C_3$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 4, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof, besides the compounds excluded hereinabove.

According to one particularly preferred embodiment of the invention, the compounds of formula (I) are chosen from the group formed by:

5,5'-(benzylazanediyl)bis(methylene)diquinolin-8-ol, 5-(((8-hydroxyquinolin-5-yl)(4-methylbenzyl)amino)methyl)quinolin-8-ol, tert-butyl 8-hydroxyquinolin-5-yl(4-methylbenzyl)carbamate, 5-(naphthalen-1-ylmethylamino)quinolin-8-ol, 5,5'-(naphthalen-1-ylmethylazanediyl)diquinolin-8-ol, tert-butyl 8-hydroxyquinolin-5-yl(naphthalen-1-ylmethyl)carbamate, and 5-(((8-hydroxyquinolin-5-yl)(4-trifluoromethyl)benzyl)amino)methyl)quinolin-8-ol.

In the context of the invention, the term "aryl" means a monocyclic or polycyclic aromatic carbon-based ring containing between 5 and 14 carbon atoms, such as phenyl, naphthyl or cresyl, and the term "heteroaryl" means an aryl comprising one or more heteroatoms chosen from N, O and S, such as pyridine, pyrimidine, pyrazine, furan, pyran, thiopyran or thiophene.

The invention also relates to the compounds of formula (I) and, preferably, pharmaceutical compositions containing them, for use as medicaments.

As mentioned previously, the Applicant has shown that such compounds show anticancer properties either by inhibiting cell proliferation and migration, or by acting via cytotoxicity. In the context of the invention, proliferation, viability and survival of cells are terms defining the antitumor properties of the compounds of formula (I).

Consequently, the invention also relates to the use of compounds of formula (I):

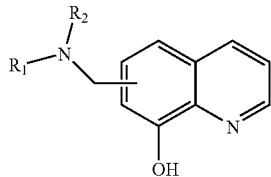

for the manufacture of a medicament intended for use as an anticancer agent,
in which formula the group —CH$_2$—NR$_1$R$_2$ is in the ortho, meta or para position relative to the —OH group, and in which
one of the radicals R$_1$ and R$_2$ represents
a hydrogen atom, a C$_1$ to C$_{10}$ alkyl group, a C$_2$ to C$_4$ alkenyl or alkynyl group or a 5-methylene-8-hydroxyquinoline group; the other represents a 5-methylene-8-hydroxyquinoline group, an aryl group, —(CH$_2$)$_n$-heteroaryl comprising one or more heteroatoms chosen from N, O and S, n being an integer between 0 and 4, a C$_4$ to C$_6$ group —(CH$_2$)$_n$-heterocycloalkyl in which the heteroatom represents N, O or S, n being an integer between 0 and 4, or alkylphenyl in which the alkyl represents C$_1$ to C$_{10}$, the phenyl group being unsubstituted or substituted with 1 or 2 halogen atoms chosen from F, Br, I and Cl or with —CF$_3$;
or one of the radicals R$_1$ and R$_2$ represents a group of formula (II) linked to the asymmetric carbon

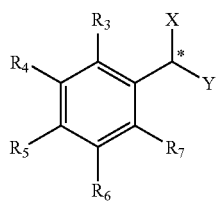

in which R$_3$, R$_4$, R$_5$, R$_6$ and R$_7$, independently of each other, represent a hydrogen atom, a C$_1$ to C$_{10}$ alkyl group, —CF$_3$, —NO$_2$, an N-5-methylene-8-hydroxyquinoline group, 1 or 2 halogen atoms chosen from F, Br, I and Cl or a group —O—R, R being a C$_1$ to C$_4$ alkyl group or —CF$_3$, X or Y represents a hydrogen atom, a C$_1$ to C$_{10}$ alkyl group, an aryl that is unsubstituted or substituted with a C$_1$ to C$_{10}$ alkyl group, —CF$_3$ or —NO$_2$,
the other of the radicals R$_1$, and R$_2$ representing an H atom, a tert-butoxycarbonyl group (Boc), 5-methylene-8-hydroxyquinoline or —(CH$_2$)$_n$-phenyl, n being an integer between 1 and 5;
or, when one of the groups R$_1$ and R$_2$ is a group Y—N—Y' in which Y is chosen from the group formed by —(CH$_2$)$_n$—, n being an integer between 1 and 10, —(CH$_2$)$_m$-phenyl-(CH$_2$)$_p$—, the phenyl being unsubstituted or substituted with 1 or 2 halogen atoms chosen from F, Br and Cl or with a C$_1$ to C$_{10}$ alkyl group, m and p being, respectively, integers between 1 and 4, and in which Y' is 5-methylene-8-hydroxyquinoline, the other represents a hydrogen atom;
or, when one of the groups R$_1$ and R$_2$ represents a group —(CH$_2$)$_n$-naphthalene, n being an integer between 1 and 10, the naphthalene group being unsubstituted or substituted with one or more groups chosen from C$_1$ to C$_{10}$ alkyl groups, —CF$_3$ and —O—R in which R is a C$_1$ to C$_{10}$ alkyl group, the other is chosen from the group formed by a hydrogen atom, a 5-methylene-8-hydroxyquinoline group and a Boc group;
or R$_1$ and R$_2$ form a piperazine that is unsubstituted or in which at least one of the carbon atoms of the ring is substituted with a C$_1$ to C$_6$ alkyl group and in which the N atom that is not part of the group —CH$_2$—NR$_1$R$_2$ is substituted with a 5-methylene-8-hydroxyquinoline group;
or R$_1$ and R$_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —(CH$_2$)$_n$-phenyl-(CH$_2$)$_n$—Z, n being an integer between 1 and 10, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof.

According to one embodiment of the invention, it is preferred to use the compounds of formula (I) for the manufacture of a medicament intended for use as an anticancer agent, in which:
one of the radicals R$_1$ and R$_2$ represents
a hydrogen atom, a C$_1$ to C$_6$ alkyl group, a C$_2$ to C$_4$ alkenyl or alkynyl group or a 5-methylene-8-hydroxyquinoline group; the other represents a 5-methylene-8-hydroxyquinoline group, an aryl group, —(CH$_2$)$_n$-heteroaryl comprising one or more heteroatoms chosen from N, O and S, n being an integer between 0 and 4, a C$_4$ to C$_6$ group —(CH$_2$)$_n$-heterocycloalkyl in which the heteroatom represents N, O or S, n being an integer between 0 and 4, or alkylphenyl in which the alkyl represents C$_1$ to C$_6$, the phenyl group being unsubstituted or substituted with 1 or 2 halogen atoms chosen from F, Br, I and Cl or with —CF$_3$;
or one of the radicals R$_1$ and R$_2$ represents a group of formula (II) linked to the asymmetric carbon

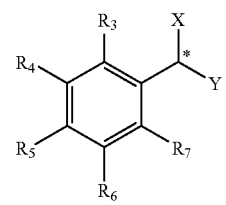

in which R$_3$, R$_4$, R$_5$, R$_6$ and R$_7$, independently of each other, represent a hydrogen atom, a C$_1$ to C$_6$ alkyl group, —CF$_3$, —NO$_2$, an N-5-methylene-8-hydroxyquinoline group, 1 or 2 halogen atoms chosen from F, Br, I and Cl or a group —O—R, R being a C$_1$ to C$_3$ alkyl group or —CF$_3$, X or Y represents a hydrogen atom, a C$_1$ to C$_6$ alkyl group, an aryl that is unsubstituted or substituted with a C$_1$ to C$_6$ alkyl group, —CF$_3$ or —NO$_2$,
the other of the radicals R$_1$ and R$_2$ representing an H atom, a Boc group, 5-methylene-8-hydroxyquinoline or —(CH$_2$)$_n$-phenyl, n being an integer between 1 and 5;
or, when one of the groups R$_1$ and R$_2$ is a group Y—N—Y' in which Y is chosen from the group formed by —(CH$_2$)$_n$—, n being an integer between 1 and 6, —(CH$_2$)$_m$-phenyl-(CH$_2$)$_p$—, the phenyl being unsubstituted or substituted with 1 or 2 halogen atoms chosen from F, Br and Cl or with a C$_1$ to $C_6$ alkyl group, m and p being, respectively, integers between 1 and 4, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 6, the naphthalene group being unsubstituted or substituted with one or more groups chosen from $C_1$ to $C_6$ alkyl groups, —$CF_3$ and —O—R in which R is a $C_1$ to $C_6$ alkyl group, the other is chosen from the group formed by a hydrogen atom, a 5-methylene-8-hydroxyquinoline group and a Boc group;

or $R_1$ and $R_2$ form a piperazine that is unsubstituted or in which at least one of the carbon atoms of the ring is substituted with a $C_1$ to $C_4$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 6, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof.

Most preferably, use is made of the compounds of formula (I) for the manufacture of a medicament intended for use as an anticancer agent, in which:

one of the radicals $R_1$ and $R_2$ represents
a hydrogen atom, a $C_1$ to $C_4$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 3, a $C_4$ to $C_6$ group —$(CH_2)_n$-heterocycloalkyl in which the heteroatom represents N, O or S, n being an integer between 0 and 3, or alkylphenyl in which the alkyl represents $C_1$ to $C_4$, the phenyl group being unsubstituted or substituted with 1 or 2 halogen atoms chosen from F and I or with —$CF_3$;

or one of the radicals $R_1$ and $R_2$ represents a group of formula (II) linked to the asymmetric carbon

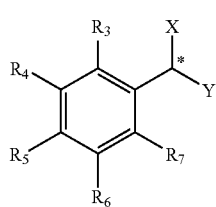

(II)

in which one of the radicals $R_3$, $R_4$, $R_5$, $R_6$ and $R_7$ represents an N-5-methylene-8-hydroxyquinoline group and the others represent a hydrogen atom, X or Y represents a hydrogen atom, a $C_1$ to $C_4$ alkyl group, an aryl that is unsubstituted or substituted with a $C_1$ to $C_4$ alkyl group, —$CF_3$ or —$NO_2$, the other of the radicals $R_1$ and $R_2$ representing an H atom, a tert-butoxycarbonyl (Boc) group or 5-methylene-8-hydroxyquinoline;

or, when one of the groups $R_1$ and $R_2$ is a group Y—N—Y' in which Y is chosen from the group formed by —$(CH_2)_n$—, n being an integer between 1 and 4, —$(CH_2)_m$-phenyl-$(CH_2)_p$—, the phenyl being unsubstituted or substituted with 1 or 2 halogen atoms chosen from F, Br and Cl or with a $C_1$ to $C_4$ alkyl group, m and p being, respectively, integers between 1 and 3, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 4, the naphthalene group being unsubstituted or substituted with one or more groups chosen from $C_1$ to $C_4$ alkyl groups, —$CF_3$ and —O—R in which R is a $C_1$ to $C_4$ alkyl group, the other is chosen from the group formed by a hydrogen atom, a 5-methylene-8-hydroxyquinoline group and a Boc group;

or $R_1$ and $R_2$ form a piperazine that is unsubstituted or in which at least one of the carbon atoms of the ring is substituted with a $C_1$ to $C_3$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 4, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof.

According to one particularly preferred embodiment of the invention, the compounds of formula (I) are used for the manufacture of a medicament intended for use as an anticancer agent, chosen from the group formed by:

5-((1,4,8,12-tetraazacyclopentadecan-8-yl)methyl)quinolin-8-ol (compound I1), tri-tert-butyl 12-((8-hydroxyquinolin-5-yl)methyl)-1,4,8,12-tetraazacyclopentadecane-1,4,8-tricarboxylate (compound I2), tri-tert-butyl 11-((8-hydroxyquinolin-5-yl)methyl)-1,4,8,12-tetraazacyclopentadecane-1,4,8-tricarboxylate (compound I3), 5-((1,4,8,11-tetraazacyclotetradecan-1-yl)methyl)quinolin-8-ol (compound I4), tri-tert-butyl 11-(3-((4,11-bis(tert-butoxycarbonyl)-8-((8-hydroxyquinolin-5-yl)methyl)-1,4,8,11-tetraazacyclotetradecan-1-yl)methyl)benzyl)-1,4,8,11-tetraazacyclotetradecane-1,4,8-tricarboxylate (compound I5), 5,5'-(propane-1,3-diylbis(azanediyl))bis(methylene) diquinolin-8-ol (compound I6), 5-((8-(4-(((1,4,8,11-tetraazacyclotetradecan-1-yl)methyl) benzyl)-1,4,8,11-tetraazacyclotetradecan-1-yl)methyl) quinolin-8-ol (compound I7), 5,5'-(piperazine-1,4-diylbis(methylene))diquinolin-8-ol (compound I8), di-tert-butyl 4,8-bis((8-hydroxyquinolin-5-yl)methyl)-1,4,8,11-tetraazacyclotetradecane-1,11-dicarboxylate (compound I9), 5,5'-(1,4,8,11-tetraazacyclotetradecane-1,11-diyl)bis(methylene)diquinolin-8-ol (compound I10), 5,5'-(1,4-phenylenebis(methylene))bis(azanediyl)bis(methylene)diquinolin-8-ol (compound I11), 5,5'-(benzylazanediyl)bis(methylene))diquinolin-8-ol (compound I12), 5-((benzylamino)methyl)quinolin-8-ol (compound I13), 5-(((8-hydroxyquinolin-5-yl)(4-methylbenzyl)amino)methyl)quinolin-8-ol (compound I14), tert-butyl 8-hydroxyquinolin-5-yl(4-methylbenzyl)carbamate (compound I15),
5-((4-methyl-benzylamino)methyl)quinolin-8-ol (compound I16),
5-(naphthalen-1-ylmethylamino)quinolin-8-ol (compound I17),
5,5'-(naphthalen-1-ylmethylazanediyl)diquinolin-8-ol (compound I18),
tert-butyl 8-hydroxyquinolin-5-yl(naphthalen-1-ylmethyl)carbamate (compound I19), and
5-(((8-hydroxyquinolin-5-yl)(4-(trifluoromethyl)benzyl)amino)methyl)quinolin-8-ol (compound I20).

Advantageously, the therapeutic activity of these compounds lies in their capacity to prevent the migration and proliferation of metastases or tumor cells, such as glioblastomas, carcinomas, sarcomas, myelomas, melanomas and mesotheliomas. In addition, the cytotoxicity induced on certain cells is also asserted.

Consequently, these compounds may be used in the treatment of many cancers chosen from the group formed by oral carcinomas, bowel carcinomas, breast carcinomas, lung carcinomas, prostate carcinomas, glioblastomas, ovarian adenocarcinomas, hepatocarcinomas and lymphoblastomas.

By way of example, the above activities of these compounds were demonstrated on different human cell lines that are tumoral or resistant to reference antitumor agents, such as oral carcinomas (KB), bowel carcinomas (HTC116, HT29 and HTC15), breast carcinomas (MCF7 and MCF7R), lung carcinomas (A549), prostate carcinomas (PC3), glioblastomas (SF268), ovarian adenocarcinomas (SK-OV-3), hepatocarcinomas (HepG2), lymphoblastomas (HL60 and K562) and on nontumoral VERO monkey kidney cells.

The compounds of the invention have the capacity to induce caspase activation, given that it is well known that caspases play an important role in apoptosis induced by a genotoxic stress and that certain drugs lead to permeabilization of the outer membrane of mitochondria, which leads to the release of cytochrome C and activation of the caspases.

The Applicant has also shown that the presence of two substituents of 5-methylene-8-hydroxyquinoline type in these compounds has a primordial influence on the anticancer activity.

Specifically, surprisingly, as shown in the examples (see later), the bis-5-methylene-8-hydroxyquinolines (compounds of formula (I) in which one of the radicals $R_1$ and $R_2$ represents a 5-methylene-8-hydroxyquinoline group) have anticancer activity that is much more pronounced than the mono-5-methylene-8-hydroxyquinoline equivalents. Specifically, it is possible to obtain IC50 values (concentration of the compounds in the reaction medium for which 50% of the tested tumor cells survived the treatment) for much lower concentrations by using bis-5-methylene-8-hydroxyquinoline compounds rather than mono-5-methylene-8-hydroxyquinoline compounds.

Without wishing to be bound by the theory that follows, it is probable that the mechanism of action of the compounds of the invention comprises the following steps of protonation of the tertiary amine (N bearing the groups $R_1$ and $R_2$), followed by an addition of a nucleophilic agent ($Nu^-$), which may be chemical or biological, to the H atom of the hydroxyquinoline group, which gives a carbanionic species, the addition being followed by resonance stabilization leading to a species known as a "quinone-methide intermediate" by cleaving the C—N bond (N bearing the groups $R_1$ and $R_2$). This intermediate would have alkylating power on chemical or biological substrates, such as nucleic acids or proteins.

A compound of formula (I) in which $R_1$ and $R_2$ independently represent a hydrogen atom, a $C_1$ to $C_{10}$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 4, a $C_4$ to $C_6$ group —$(CH_2)_n$-heterocycloalkyl in which the heteroatom represents N, or S, n being an integer between 0 and 4, or alkylphenyl in which the alkyl represents $C_1$ to $C_{10}$, the phenyl group being unsubstituted or substituted with 1 or 2 halogen atoms chosen from F, Br, I and Cl or with —$CF_3$, may be prepared via processes known to those skilled in the art, and in particular according to the synthesis described in the publication by J. H. Burckhalter et al., J. Org. Chem., 1961, vol. 26, pp. 4078-4083.

In summary, the starting material to be considered is 5-chloromethyl-8-hydroquinoline hydrochloride, which is suspended in a suitable solvent, such as ethyl acetate. The appropriate aminated compounds for defining the groups $R_1$ and $R_2$ above are added to this suspension.

By way of example, mention may be made of amines comprising $C_1$ to $C_{10}$ alkanes, a $C_4$ to $C_6$ group —$(CH_2)_n$-heterocycloalkyl in which the heteroatom represents N, O or S, a $C_2$ to $C_4$ alkenyl or alkynyl group, an aryl group, a group —$(CH_2)_n$-heteroaryl comprising one or more heteroatoms chosen from N, O and S, n being an integer between 0 and 4, alkylphenyl, the phenyl group being unsubstituted or substituted with 1 or 2 halogen atoms chosen from F, Br, I and Cl or with —$CF_3$, and a 5-methylene-8-hydroxyquinoline group. The mixture obtained is heated on a water bath with gentle stirring. The reaction product is then filtered and washed with the solvent, which is then removed by evaporation. The residue thus obtained is then recrystallized from a solvent of alkane type, such as petroleum ether.

The preparation of a compound of formula (I) in which, firstly, one of the radicals $R_1$ and $R_2$ represents a group of formula (II) in which $R_3$, $R_4$, $R_5$, $R_6$ and $R_7$, independently of each other, represent a hydrogen atom, a $C_1$ to $C_{10}$ alkyl group, —$CF_3$, —$NO_2$, an N-5-methylene-8-hydroxyquinoline group, 1 or 2 halogen atoms chosen from F, Br, I and Cl or a group —O—R, R being a $C_1$ to $C_4$ alkyl group or —$CF_3$, X or Y represents a hydrogen atom, a $C_1$ to $C_{10}$ alkyl group, an aryl that is unsubstituted or substituted with a $C_1$ to $C_{10}$ alkyl group, —$CF_3$ or —$NO_2$,
the other of the radicals $R_1$ and $R_2$ representing H, a tert-butoxycarbonyl (Boc) group, 5-methylene-8-hydroxyquinoline or —$(CH_2)_n$-phenyl, n being an integer between 1 and 5; and
secondly, when one of the groups $R_1$ and $R_2$ represents a group —$(CH_2)_n$-naphthalene, the naphthalene group being unsubstituted or substituted with one or more groups chosen from $C_1$ to $C_{10}$ alkyl groups, —$CF_3$ and —O—R in which R is a $C_1$ to $C_{10}$ alkyl group, n being an integer between 1 and 10, the other is chosen from the group formed by a hydrogen atom, a 5-methylene-8-hydroxyquinoline group and a tert-butoxycarbonyl (Boc) group,
may be performed according to processes known in the prior art.

By way of example, two methodologies may be used for the preparation of the various compounds mentioned above:

Methodology 1: the precursor amino substrate, corresponding to the compounds for defining the groups $R_1$ and $R_2$ above, is reacted with 5-chloromethyl-8-hydroxyquinoline in acetonitrile, in the presence of a weak mineral base, such as $K_2CO_3$. After filtration and evaporation, the residue is washed with a citric acid solution and the aqueous phase is extracted several times with a suitable solvent, such as ethyl acetate, and is then dried over magnesium sulfate, and then evaporated. The compounds mono- and disubstituted with the 8-hydroxyquinoline group derived from the condensation are then separated out and isolated by chromatographic separation on silica gel, using various mixtures of solvents commonly used in this chromatography, such as methylene chloride, various alkanes, in particular isooctane, and isopropyl ether.

Methodology 2 for Separation by Protection/Deprotection

The separation of the derivatives mono- and disubstituted with 8-hydroxyquinoline groups is performed after a step of protection with a tert-butoxycarbonyl (Boc) group. After a step of protection of the monosubstituted derivative, the disubstituted derivative, which is more polar, is readily separated from the derivative monosubstituted with the Boc group by chromatography on silica gel. The isolated monosubstituted derivative protected with the Boc group is then deprotected in acidic medium in a manner known to those skilled in the art. The protected mono derivative is obtained in hydrochloride form, which is isolated by precipitation from ethyl ether, and isolated pure after filtration.

The isolated compounds are then identified by NMR spectroscopy ($^1$H and $^{13}$C) and by mass spectrometry.

In the case where, in the compound of formula (I), one of the groups $R_1$ and $R_2$ is a group Y—N—Y' in which Y is —$(CH_2)_n$—, n being an integer between 1 and 10, and in which Y' is 5-methylene-8-hydroxyquinoline, the other represents a hydrogen atom, and $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 10, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof, these compounds may be prepared according to the various synthetic routes described in the publication by V. Moret et al., Bioorganic & Medicinal Chemistry Letters, 16, 2006, pp. 5988-5992.

More specifically, when $R_1$ and $R_2$ form a polyazamacrocycle representing a 1,4,8,11-tetraazacyclotetradecane group, one of the N atoms of the ring in position 1, 4 and 8 being, independently, substituted with —$(CH_2)_n$-phenyl-$(CH_2)_n$—Z, n being an integer between 1 and 10, in which Z represents one of the N atoms of a 1,4,8,12-tetraazacyclopentadecane in which the other N atoms of the ring in position 1, 4 and 8 are unsubstituted or are each independently substituted with a Boc group, the synthesis is performed in the following manner.

The starting material is 1,4,8,11-tetraazacyclotetradecane (3 equivalents), which is reacted with di-tert-butyl dicarbonate (1 equivalent) in the presence of methylene chloride, at room temperature, overnight. After chromatographic purification, the product 1,11-di-tert-butoxy-1,4,8,11-tetraazacyclotetradecane is obtained. It is possible to promote tri- or tetra-protection of the nitrogen atom of the cyclam with the Boc group, according to the methodology described in Dessolin J. et al., J. Med. Chem., 1999, 42, 229-241. In summary, selective tri-protection of the cyclam or bicyclam derivative with Boc groups is obtained by using 1.8 equivalents of the di-tert-butoxycarbonyl reagent per 1 equivalent of cyclam in methylene chloride, as indicated above. In this case, triple protection of the cyclam with Boc is predominant relative to the mono-, di- and tetra-protected compounds.

In addition, a 1,4,8,11-tetraazacyclotetradecane compound (1 equivalent) in which one of the nitrogen atoms is substituted with a Boc group undergoes a condensation reaction with the compound Br—$(CH_2)_n$-phenyl-$(CH_2)_n$—Br (1 equivalent) in the presence of a weak base, such as $K_2CO_3$, in dimethylformamide (DMF), for three days, at room temperature. The reaction allows grafting of $(CH_2)_n$-phenyl-$(CH_2)_n$—Br onto a free nitrogen (not substituted with a Boc group). The product thus obtained is reacted with 1,11-di-tert-butoxy-1,4,8,11-tetraazacyclotetradecane in acetonitrile in the presence of a weak base, such as $K_2CO_3$. Next, the latter intermediate product is reacted with 5-chloromethyl-8-hydroxyquinoline in acetonitrile in the presence of a weak base, such as $K_2CO_3$.

The compound of formula (I) in which $R_1$ and $R_2$ form a polyazamacrocycle (cyclam) representing a 1,4,8,11-tetraazacyclotetradecane group in which at least one of the N atoms of the ring in position 1, 4 and 8 is substituted with —$(CH_2)_n$-phenyl-$(CH_2)_n$—Z in which Z represents one of the N atoms of a 1,4,8,11-tetraazacyclotetradecane, the other nitrogen atoms being substituted with a Boc group, is thus obtained.

The Boc groups present on these compounds may be removed by placing these compounds in contact in an acidic medium, in the presence of ethyl ether and at a temperature of between 25° C. and 70° C., according to standard procedures. Deprotection of the protected derivative is performed in acidic medium, the mono-protected derivative is thus obtained in hydrochloride form, which is isolated by precipitation from ethyl ether, and isolated pure after filtration.

The synthesis is performed in the same manner when $R_1$ and $R_2$ form a polyazamacrocycle (cyclam) representing a 1,4,8,11-tetraazacyclopentadecane group, at least one of the N atoms of the ring in position 1, 4 and 8 being substituted with —$(CH_2)_n$-phenyl-$(CH_2)_n$—Z, n being an integer between 1 and 10, in which Z represents a 1,4,8,11-tetraazacyclopentadecane group in which the other N atoms of the ring in position 1, 4 and 8 are unsubstituted or are each independently substituted with a Boc group.

When, in the compound of formula (I), $R_1$ and $R_2$ form a piperazine that is unsubstituted or in which at least one of the carbon atoms of the ring is substituted with a $C_1$ to $C_6$ alkyl group and in which the other N atom is substituted with a 5-methylene-8-hydroxyquinoline group, and when, in the compound of formula (I), one of the groups $R_1$ and $R_2$ is a group Y—N—Y' in which Y is —$(CH_2)_n$—, n being an integer between 1 and 10, and in which Y' is 5-methylene-8-hydroxyquinoline, the other represents a hydrogen atom, such compounds may be prepared as follows.

A condensation reaction of 5-chloromethyl-8-hydroxyquinoline with a piperazine that is unsubstituted or in which at least one of the carbon atoms of the ring is substituted with a $C_1$ to $C_6$ alkyl group, or in the presence of $CH_3$—$(CH_2)_{n-1}$—N—$(CH_2)_{n-1}$—$CH_3$ in acetonitrile in the presence of a weak base, such as $K_2CO_3$, at a temperature of between 25° C. and 70° C., overnight, is performed.

The compounds of formula (I) in which $R_1$ and $R_2$ form a polyazamacrocycle representing a 1,4,8,12-tetraazacyclopentadecane group that is unsubstituted or in which one of the N atoms of the ring in position 1, and 8 is substituted with a Boc group, may be prepared by reacting 1,4,8,12-tetraazacyclopentadecane that is unsubstituted or in which one of the N atoms of the ring in position 1, 4 and 8 is substituted with a Boc group with 5-chloromethyl-8-hydroxyquinoline in chloroform or methylene chloride in the presence of an excess of diisopropylethylamine, overnight, at a temperature of between 25° C. and 70° C. Such compounds in which the Boc group is absent are obtained by placing these compounds in contact in an acidic medium, in the presence of ethyl ether and at a temperature of between 25° C. and 70° C., according to standard procedures defined hereinabove.

The compounds of formula (I) in which $R_1$ and $R_2$ form a polyazamacrocycle representing a 1,4,8,12-tetraazacyclopentadecane group, one of the N atoms of the ring in position 1, 4 and 8 being substituted with a Boc group and another N atom is substituted with a 5-methylene-8-hydroxyquinoline group are advantageously synthesized as indicated above.

When $R_1$ and $R_2$ form a 5- or 6-membered cyclic polyamine,
in the case where one of the groups $R_1$ and $R_2$ is —$(CH_2)_m$-phenyl-$(CH_2)_p$—, the phenyl being unsubstituted or substituted with 1 or 2 halogen atoms chosen from F, Br and Cl or with a $C_1$ to $C_6$ alkyl group, m and p being, respectively, numbers between 1 and 4, and in which Y' is 5-methylene-8-hydroxyquinoline, the other represents a hydrogen atom, and when $R_1$ and $R_2$ form a 4- to 8-membered aliphatic ring that is unsubstituted or substituted with a $C_1$ to $C_6$ alkyl group or with a group —O—R in which R is a $C_1$ to $C_{10}$ alkyl group, or an aryl, optionally hydrogenated, which is unsubstituted or substituted with a $C_1$ to $C_6$ alkyl group or with a halogen atom chosen from F, Br and Cl, such compounds may be prepared according to Methodology 1 or according to the publication by Moret et al. mentioned above, using a condensation reaction of 5-chloromethyl-8-hydroxyquinoline in chloroform or methylene chloride on a free amine function of an amino compound bearing the groups $R_1$ and $R_2$ above. This reaction is performed in the presence of a weak base, such as $K_2CO_3$, at a temperature of between 25° C. and 70° C., preferably in the region of 70° C.

The tests for evaluating the anticancer properties of these compounds are performed taking the following cell lines into consideration.

For the U-87/GFP cells, the control of cell proliferation and migration in the presence of the compounds (I) of the invention is performed via a calorimetric method (MTS) and is performed according to known standard protocols. The methodologies implemented use flash cytometry (Trophos S.A., Marseilles, France). The flash cytometry technique involves fluorescence, which consists in irradiating a compound at a set wavelength and in recording the fluorescence emitted at another wavelength. This technique is performed with a flash cytometer and adapted for 96-well test plates. The excitation and emission wavelengths in the context of use of this fluorescence are located in the 485-495 nm range. The measured fluorescence expresses the amount of cells surviving after treatment with the compounds of the invention. The publications by Luby-Phelps K. et al., J. Histochemistry and Cytometry, 2003, 51, 271-274 and Modarai B. et al., Circulation, 2005, 111, 2645-2653 may be mentioned by way of reference for the above methods.

The determination of the antimigratory activity of the compounds (I) of the invention on these same cell lines, cultured in MEM medium (Minimum Essential Medium) is performed via the "scratch" technique that consists in scratching a cell lawn using a micropipette cone. By comparison with these same cells not containing the compounds of the invention, the antimigratory effect is determined. A 100% migration is attributed to the untreated cells, whereas, as a function of the concentration of the compounds (I) of the invention, total stoppage of migration is determined by observation of the "scratch" remaining unfilled by the cell migration, by means of computer software.

The cells of the U87/GFP lines are cultured in 96-well plates according to a standard methodology described by Bajetto et al., Neurochemistry International, 2006, 43, 31-38 in the presence of different concentrations of the compounds of the invention.

The cell proliferation is determined and quantified according to standard methods known to those skilled in the art. A 100% proliferation is attributed to the untreated cells and a percentage less than 100% is obtained when the same cells are treated with the compounds of the invention.

The cell proliferation and migration are determined by imaging using a flash cytometer (Trophos S.A., Marseilles, France), and the calculations are performed using the "Metamorph 4.6" imaging signal processing software (Molecular Devices, USA), the use of which, which is known in the field, makes it possible to determine the above two effects independently of each other.

Cancerous KB cells are also considered, to determine the cell viability (or survival rate). This cell viability is determined according to the teaching of Nicholson K. M. et al., British Journal of Cancer, 1999, 81, 423-430.

KB cells are human carcinoma cell lines, KB-3-1. These cells are maintained in a culture medium, "Dulbecco's modified Eagle's medium" (DMEM-Sigma), which contains 0.11 g/l of sodium pyruvate and 4.5 g/l of glucose, supplemented with 10% (v/v) fetal calf serum, penicillin (32 µg/ml) and streptomycin (50 µg/ml). The cells are cultured as monolayers and are incubated at 37° C. in a humid atmosphere (95% air/5% $CO_2$).

The preceding KB cells are then incubated in 6- or 96-well plates in the presence of the test compounds of the invention, dissolved in dimethyl sulfoxide (DMSO). The content of surviving cells is measured by the "colony-forming assay" test, in which the cells are redistributed at a density of 100 to 300 cells per well in 24-well plates, for a period of 8 days, and are then stained with Leishman's reagent (0.2% in methanol). The colonies of more than 50 cells are counted visually under a microscope, the survival rate being expressed on the colonies formed in the presence of the compounds of the invention relative to cell colonies not treated with said compounds. The determination of the IC50 values (concentration of compounds in the reaction medium for which 50% of the tested tumor cells survived the treatment) enables comparison of the efficacy of these compounds.

During the two cell proliferation and cell migration tests, commonly-used anticancer derivatives serve as reference derivatives.

By way of example, 5-((8-(4-((1,4,8,11-tetraazacyclotetradecan-1-yl)methyl)benzyl)-1,4,8,11-tetraazacyclotetradecan-1-yl)methyl)quinolin-8-ol (compound I7) and di-tert-butyl 4,8-bis((8-hydroxyquinolin-5-yl)methyl)-1,4,8,11-tetraazacyclotetradecane-1,11-dicarboxylate (compound I9) have, respectively, a cytotoxic activity IC50, on KB cells, corresponding to a concentration of about 0.1 µM and about 0.4 µM. These two compounds also have antiproliferative activity on U87/GFP cells that is observed at 2 µM.

The Applicant even observed that, for certain compounds (I) of the invention, it is possible to obtain IC50 values of nanomolar order on KB cells, which demonstrates that the compounds (I) of the invention are highly efficient anticancer agents.

EXAMPLES

Example 1

This example gives interim results illustrating the capacities of the compounds of the invention for inhibiting the proliferation and migration of cells of the U-87/GFP lines (inhibition expressed as a percentage) and the viability of KB cells (cytotoxicity measurement) using the procedures described above.

Table 1 gives percentage values associated with concentrations of compounds of formula (I), relative to a reference example not containing the compounds of the invention. The higher the percentage for the lowest possible concentration of compounds (I) of the invention, the greater the capacity of the compounds of the invention to inhibit cell viability on KB cells.

TABLE 1

| Compounds | Cytotoxicity on KB cells | Antiproliferative effect on U87/GFP cells | Antimigratory effect on U87/GFP cells |
|---|---|---|---|
| A* | Inactive at 10 µM | Inactive at 50 µM | Inactive at 50 µM |
| B* | Inactive at 10 µM | Inactive at 50 µM | Inactive at 50 µM |
| Temodal ® | nd | 10 µM/50% | 10 µM/50% |
| I2 | 28% at 1 µM | nd | |
| I3 | 15% at 1 µM | nd | |
| I4 | 27% at 1 µM | nd | |
| I7 | 93% at 1 µM | 2 µM | |
| I8 | 94% at 1 µM | nd | |
| I9 | 77% at 1 µM | 10 µM | |
| I12 | 93% at 1 µM | 0.5 µM/30% | 2 µM/80% |
| I13 | 90% at 1 µM | 10 µM/50% | — |
| I14 | 90% at 1 µM | 0.5 µM/65% | 0.5 µM/40% |
| I16 | 50% at 2 µM | 2 µM/80% | 2 µM/80% |
| I18 | — | 2 µM/50% | — |
| I20 | — | 0.1 µM/80% | 0.2 µM/40% |

*A and B: commercially available compounds
nd: not determined

For other compounds of formula (I), the following results are obtained (Tables 2 and 2a).

TABLE 2

| R₁ | R₂ | Compound | Antiproliferative effect on U87/GFP cells |
|---|---|---|---|
| 5-methyl-8-hydroxyquinoline | 5-methyl-8-hydroxyquinoline | I21 | >10 µM/50% |
| 5-methyl-8-hydroxyquinoline | tetrahydrofuran-2-ylmethyl | I22 | 1 µM/50% |
| 5-methyl-8-hydroxyquinoline | thiophen-2-ylmethyl | I23 | 0.2 µM/50% |
| 5-methyl-8-hydroxyquinoline | 4-(trifluoromethoxy)benzyl | I24 | — |

TABLE 2-continued

| R₁ | R₂ | Compound | Antiproliferative effect on U87/GFP cells |
|---|---|---|---|
| 5-ethyl-8-hydroxyquinoline | 2-ethyl-1-methylpyrrole | I25 | 2 µM/50% |
| 5-ethyl-8-hydroxyquinoline | propyl-pyrrolidine | I26 | 10 µM/50% |
| 5-ethyl-8-hydroxyquinoline | 3-iodoethylbenzene | I27 | 2 µM/50% |
| ethylbenzene | ethylbenzene | I28 | 2 µM/50% |

TABLE 2a $R_1$: 5-ethyl-8-hydroxyquinoline

| | $R_2$: group of formula (II) | Compound | Antiproliferative effect on U87/GFP cells |
|---|---|---|---|
| Id | X and Y = H<br>$R_3, R_4, R_6,$<br>$R_7 = H$<br>$R_5 = NO_2$ | I29 | 1 µM/60% |
| Id | X and Y = H<br>$R_3, R_4, R_5,$<br>$R_6 = H$<br>$R_7 = CF_3$ | I30 | 0.5 µM/60% |
| Id | X = H<br>Y = CH₃<br>$R_3, R_4, R_6,$<br>$R_7 = H$<br>$R_5 = CH_3$ | I31 | >10 µM/50% |
| Id | X and Y = H<br>$R_3, R_4, R_5,$<br>$R_7 = H$<br>$R_6 = CF_3$ | I32 | 0.2 µM/50% |
| H | X = H<br>Y = CH₃<br>$R_3$ to $R_7 = H$ | I33 | 0.5 µM/50% |
| H | X and Y = H<br>$R_3, R_4, R_6,$<br>$R_7 = H$<br>$R_5 = CF_3$ | I34 | 5-10 µM/50% |
| H | X and Y = H<br>$R_3, R_4, R_5,$<br>$R_7 = H$<br>$R_6 = CF_3$ | I35 | — |
| Boc | X and Y = H<br>$R_3, R_4, R_5,$<br>$R_7 = H$<br>$R_6 = CF_3$ | I36* | 5-10 µM/50% |
| Boc | X and Y = H<br>$R_3, R_4, R_6,$<br>$R_7 = H$<br>$R_5 = CF_3$ | I37 | 5-10 µM/50% |
| Boc | X and Y = H<br>$R_3$ to $R_7 = H$ | I38 | 5-10 µM/50% |

Id: idem
*: for I36, an antimigratory effect is observed on the same cells: 2 µM/40%

The commercially available compounds A and B do not show any capacity for inhibiting the cell viability, at a concentration of 10 µM on KB cells. This inactivity is even greater on U87/GFP cells. In addition, this example shows that the compounds of the invention have better overall efficacy than Temodal® for the in vitro antiproliferative activity on U87/GFP cells.

Example 2

From the results obtained in Example 1, it was possible to determine the IC50 values on the KB cell lines (Table 3), according to the protocol described previously.

For the measurement of the cytotoxicity effect on KB cells, two experiments were performed in parallel.

TABLE 3

| Compounds | Cytotoxicity on KB cells |
|---|---|
| I7 | 0.122/0.303 µM |
| I8 | 0.043/0.032 µM |
| I9 | 0.398/0.639 µM |
| I12 | 0.0015/0.005 µM |
| I13 | >1.0/1.3 µM |
| I14 | 0.0026/0.0014 µM |
| I16 | 11/10 µM |
| I17 | 1.0/0.95 µM |
| I18 | 0.005/0.0045 µM |
| I20 | 0.0013/0.0015 µM |
| I29 | 0.042/0.037 µM |
| I30 | 0.123/0.135 µM |
| I31 | 0.041/0.052 µM |
| I33 | 1.0/1.1 µM |
| I34 | 10 µM/9 µM |
| I35 | 0.20 µM/0.22 µM |
| I36 | 1.0/1.1 µM |
| I37 | 8 µM/9 µM |
| I38 | 0.9/1.1 µM |

Table 3 indicates that it is possible to obtain cell cytotoxicity, expressed by the IC50 value, for concentrations of nanomolar order, although values of the order of about ten micromoles are still acceptable.

When the compounds containing two 5-methylene-8-hydroxyquinoline groups (bis-5-methylene-8-hydroxyquinolines) are compared with the compounds containing only one such group (mono-5-methylene-8-hydroxyquinolines), such as compounds I12, I14 and I20 relative to I13, I16 and I34, it is noted that the bis-5-methylene-8-hydroxyquinoline derivatives are much more active than the mono-5-methylene-8-hydroxyquinoline equivalents, all factors being otherwise equal.

From these examples, the Applicant showed that, for compounds of formula (I) in which $R_1$ is a 5-methylene-8-hydroxyquinoline group and $R_2$ is a group (II) in which X and Y represent an H atom, or X is H and Y is —$CH_3$, $R_3$ to $R_7$ have different substituents, the nature and position of these substituents have an influence on their activity.

If compounds I12, I14, I20, I29, I30 and I31 are considered, it is seen that the —$CF_3$ group para to the phenyl ring (I20) confers greater anticancer activity on the compound than when this para position is occupied either by —$NO_2$ (I29) or —$CH_3$ (I14). Moreover, the para position for the —$CF_3$ group (I20) is much more favorable in terms of activity than when this group occupies the ortho position (I30). When one of the groups X and Y is methyl, a reduction in the anticancer activity is observed, which nevertheless remains very acceptable (I14 and I31).

Example 3

This example is intended to show that the compounds of the invention also have antitumor activities on different cell lines mentioned previously.

Table 4 presents the results of the IC50 (cytotoxicity) on different cell lines, according to the protocol described previously, obtained for compounds I14 and I20.

TABLE 4

| | Cytotoxicity (nM) | |
|---|---|---|
| Cells | I20 | I14 |
| HTC116 | 1.5 ± 0.1 | 3.2 ± 1.2 |
| HTC15 | 0.8 ± 1.0 | 6.0 ± 7.3 |
| MCF7 | 1.2 ± 0.3 | 5.4 ± 0.9 |
| MCF7R | 4.7 ± 1.3 | 37.3 ± 28 |
| OV3 | 3.0 ± 0.1 | 8.0 ± 0.4 |
| PC3 | 206 ± 113 | 343 ± 125 |
| A549 | 0.9 ± 0.2 | 4.3 ± 0.1 |
| SF268 | 91 ± 49 | 178 ± 83 |
| HL60 | 10.9 ± 4.9 | 32.7 ± 6.6 |
| K562 | 5.2 ± 8.2 | 40.8 ± 22 |
| HepG2 | 22.8 ± 39.2 | 52.1 ± 14.5 |

These results indicate that the compounds of the invention have established anticancer activity in the treatment of various tumor cells.

A study of toxicity on mice showed that the LD50 value for the derivative I20 is 100 mg/kg, which demonstrates relatively low toxicity for the derivative I20, given that for anticancer drugs such as Taxol, the LD50 in mice is about 10 mg/kg.

Example 4

This example is intended to show that the cytotoxic activity of the compounds of the invention on HL60 cell lines (lymphoblastomas) depends on the induction of caspases.

In this example, in order to show the role of compounds I14 and I20 in this effect, specific products were used: DEVD for caspases 3/7, IEDT for caspases 8, and LEHD for caspases 9. Moreover, colchicine was used as reference compound that induces this activity of caspases. I14 and I20 were tested at three concentrations: 1 µM, 0.1 µM and 0.01 µM.

The experiments were performed by placing I14 and I20 in contact with HL60 cells for 48 hours, according to the standard protocol described by Margolin et al., J. Biol. Chem. (1997), 272, p. 7223, using standard commercially available diagnostic kits (Calbiochem, USA).

The results obtained show that neither I14 nor I20 has an effect on the activation of caspases 3/7 at a concentration of 0.01 µM, but they show a strong effect at the other two concentrations (1 µM and 0.1 µM). However, I14 and I20 have no effect on the activation of caspases 8 and 9 at the above concentrations.

The invention claimed is:
1. A compound of formula (I):

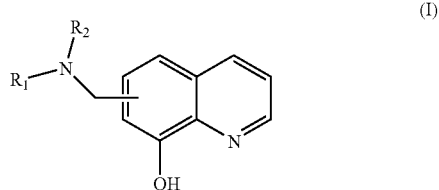

the group —$CH_2$—$NR_1R_2$ being in the ortho, meta or para position relative to the —OH group, in which:

one of the radicals $R_1$ and $R_2$ represents a hydrogen atom, a $C_1$ to $C_{10}$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 4, a $C_4$ to $C_6$ group —$(CH_2)_n$-heterocycloalkyl in which the heteroatom represents N, O or S, n being an integer between 0 and 4, or alkylphenyl in which the alkyl represents $C_1$ to $C_{10}$, the phenyl group being unsubstituted or substituted with 1 or 2 halogen atoms chosen from F, Br, I and Cl or with —$CF_3$;

or one of the radicals $R_1$ and $R_2$ represents a group of formula (II) linked to the asymmetric carbon

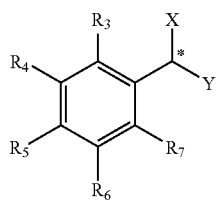

(II)

in which $R_3$, $R_4$, $R_5$, $R_6$ and $R_7$, independently of each other, represent a hydrogen atom, a $C_1$ to $C_{10}$ alkyl group, —$CF_3$, —$NO_2$, an N-5-methylene-8-hydroxyquinoline group, 1 or 2 halogen atoms chosen from F, Br, I and Cl or a group —O—R, R being a $C_1$ to $C_4$ alkyl group or —$CF_3$, X or Y represents a hydrogen atom, a $C_1$ to $C_{10}$ alkyl group, an aryl that is unsubstituted or substituted with a $C_1$ to $C_{10}$ alkyl group, —$CF_3$ or —$NO_2$, the other of the radicals $R_1$ and $R_2$ representing an H atom, a tert-butoxycarbonyl group (Boc), 5-methylene-8-hydroxyquinoline or —$(CH_2)_n$-phenyl, n being an integer between 1 and 5;

or, when one of the groups $R_1$ and $R_2$ is a group Y—N—Y' in which Y is chosen from the group formed by —$(CH_2)_n$—, n being an integer between 1 and 10, —$(CH_2)_m$-phenyl-$(CH_2)_p$—, the phenyl being unsubstituted or substituted with 1 or 2 halogen atoms chosen from F, Br and Cl or with a $C_1$ to $C_{10}$ alkyl group, m and p being, respectively, integers between 1 and 4, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 10, the naphthalene group being unsubstituted or substituted with one or more groups chosen from $C_1$ to $C_{10}$ alkyl groups, —$CF_3$ and —O—R in which R is a $C_1$ to $C_{10}$ alkyl group, the other is chosen from the group formed by a hydrogen atom, a 5-methylene-8-hydroxyquinoline group and a Boc group;

or $R_1$ and $R_2$ form a piperazine in which at least one of the carbon atoms of the ring is substituted with a $C_1$ to $C_6$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 10, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof, with the exclusion of 5-((benzylamino)methyl)quinolin-8-ol, and 5-((1,4,8,12-tetraazacyclopentadecan-8-yl)methyl)quinolin-8-ol, tri-tert-butyl 12-((8-hydroxyquinolin-5-yl)methyl)-1,4,8,12-tetraazacyclopentadecane-1,4,8-tricarboxylate, tri-tert-butyl 11-((8-hydroxyquinolin-5-yl)methyl)-1,4,8,11-tetraazacyclotetradecane-1,4,8-tricarboxylate, 5-((1,4,8,11-tetraazacyclotetradecan-1-yl)methyl)quinolin-8-ol, tri-tert-butyl 11-(3-((4,11-bis(tert-butoxycarbonyl)-8-((8-hydroxyquinolin-5-yl)methyl)-1,4,8,11-tetraazacyclotetradecan-1-yl)methyl)benzyl)-1,4,8,11-tetraazacyclotetradecane-1,4,8-tricarboxylate, 5,5'-(propane-1,3-diylbis(azanediyl))bis(methylene)-diquinolin-8-ol, 5-((8-(4-((1,4,8,11-tetraazacyclotetradecan-1-yl)methyl)benzyl)-1,4,8,11-tetraazacyclotetradecan-1-ylmethyl)quinolin-8-ol, di-tert-butyl 4,8-bis((8-hydroxyquinolin-5-yl)methyl)-1,4,8,11-tetraazacyclotetradecane-dicarboxylate, 5,5'-(1,4,8,11-tetraazacyclotetradecane-1,1'-diyl)bis(methylene)diquinolin-8-ol, 5,5'-(1,4-phenylenebis(methylene))bis(azanediyl)-bis(methylene)diquinolin-8-ol, 5-(((8-hydroxyquinolin-5-yl)(4-methylbenzyl)amino)-methyl)quinolin-8-ol, tert-butyl 8-hydroxyquinolin-5-yl(4-methylbenzyl)-carbamate, 5-((4-methylbenzylamino)methyl)quinolin-8-ol, 5-(naphthalen-1-ylmethylamino)quinolin-8-ol, 5,5'-(naphthalen-1-ylmethylazanediyl)diquinolin-8-ol, tert-butyl 8-hydroxyquinolin-5-yl(naphthalen-1-ylmethyl)carbamate, and 5-(((8-hydroxyquinolin-5-yl)(4-(trifluoromethyl)benzyl)amino)methyl)quinolin-8-ol.

2. The compound according to claim 1, in which:

one of the radicals $R_1$ and $R_2$ represents a hydrogen atom, a $C_1$ to $C_6$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 4, a $C_4$ to $C_6$ group —$(CH_2)_n$-heterocycloalkyl in which the heteroatom represents N, O or S, n being an integer between 0 and 4, or alkylphenyl in which the alkyl represents $C_1$ to $C_6$, the phenyl group being unsubstituted or substituted with 1 or 2 halogen atoms chosen from F, Br, I and Cl or with —$CF_3$;

or one of the radicals $R_1$ and $R_2$ represents a group of formula (II) linked to the asymmetric carbon

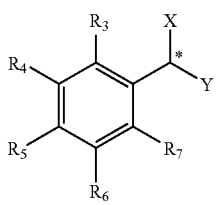

(II)

in which $R_3$, $R_4$, $R_5$, $R_6$ and $R_7$, independently of each other, represent a hydrogen atom, a $C_1$ to $C_6$ alkyl group, —$CF_3$, —$NO_2$, an N-5-methylene-8-hydroxyquinoline group, 1 or 2 halogen atoms chosen from F, Br, I and Cl or a group —O—R, R being a $C_1$ to $C_3$ alkyl group or —$CF_3$, X or Y represents a hydrogen atom, a $C_1$ to $C_6$ alkyl group, an aryl that is unsubstituted or substituted with a $C_1$ to $C_6$ alkyl group, —$CF_3$ or —$NO_2$, the other of the radicals $R_1$ and $R_2$ representing an H atom, a Boc group, 5-methylene-8-hydroxyquinoline or —$(C_{1-2})_n$-phenyl, n being an integer between 1 and 5;

or, when one of the groups $R_1$ and $R_2$ is a group Y—N—Y' in which Y is chosen from the group formed by — $(CH_2)_n$—, n being an integer between 1 and 6, —$(CH_2)_n$-phenyl-$(CH_2)_p$—, the phenyl being unsubstituted or substituted with 1 or 2 halogen atoms chosen from F, Br and Cl or with a $C_1$ to $C_6$ alkyl group, m and p being, respectively, integers between 1 and 4, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 6, the naphthalene group being unsubstituted or substituted with one or more groups chosen from $C_1$ to $C_6$ alkyl groups, —$CF_3$ and —O—R in which R is a $C_1$ to $C_6$ alkyl group, the other is chosen from the group formed by a hydrogen atom, a 5-methylene-8-hydroxyquinoline group and a Boc group;

or $R_1$ and $R_2$ form a piperazine that is unsubstituted or in which at least one of the carbon atoms of the ring is substituted with a $C_1$ to $C_4$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)$—Z, n being an integer between 1 and 6, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof, besides the compounds excluded in claim 1.

3. The compound according to claim 1, in which:

one of the radicals $R_1$ and $R_2$ represents a hydrogen atom, a $C_1$ to $C_4$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 3, a $C_4$ to $C_6$ group —$(CH_2)_n$-heterocycloalkyl in which the heteroatom represents N, O or S, n being an integer between 0 and 3, or alkylphenyl in which the alkyl represents $C_1$ to $C_4$, the phenyl group being unsubstituted or substituted with 1 or 2 halogen atoms chosen from F and I or with —$CF_3$;

or one of the radicals $R_1$ and $R_2$ represents a group of formula (II) linked to the asymmetric carbon

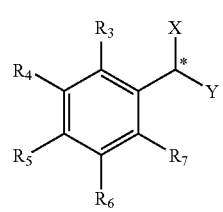

(II)

in which one of the radicals $R_3$, $R_4$, $R_5$, $R_6$ and $R_7$ represents an N-5-methylene-8-hydroxyquinoline group and the others represent a hydrogen atom, X or Y represents a hydrogen atom, a $C_1$ to $C_4$ alkyl group, an aryl that is unsubstituted or substituted with a $C_1$ to $C_4$ alkyl group, —$CF_3$ or —$NO_2$, the other of the radicals $R_1$ and $R_2$ representing H, a tert-butoxycarbonyl (Boc) group or 5-methylene-8-hydroxyquinoline;

or, when one of the groups $R_1$ and $R_2$ is a group Y—N—Y' in which Y is chosen from the group formed by — $(CH_2)_n$—, n being an integer between 1 and 4, —$(CH_2)_m$-phenyl-$(CH_2)_p$—, the phenyl being unsubstituted or substituted with 1 or 2 halogen atoms chosen from F, Br and Cl or with a $C_1$ to $C_4$ alkyl group, m and p being, respectively, integers between 1 and 3, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 4, the naphthalene group being unsubstituted or substituted with one or more groups chosen from $C_1$ to $C_4$ alkyl groups, —$CF_3$ and —O—R in which R is a $C_1$ to $C_4$ alkyl group, the other is chosen from the group formed by a hydrogen atom, a 5-methylene-8-hydroxyquinoline group and a Boc group;

or $R_1$ and $R_2$ form a piperazine in which at least one of the carbon atoms of the ring is substituted with a $C_1$ to $C_3$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 4, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof.

4. The compound according to claim 1, wherein said compound is:
5,5'-(benzylazanediyl)bis(methylene)diquinolin-8-ol,
5-(((8-hydroxyquinolin-5-yl)(4-methylbenzyl)amino)methyl)quinolin-8-ol,
tert-butyl 8-hydroxyquinolin-5-yl(4-methylbenzyl)carbamate,
5-(naphthalen-1-ylmethylamino)quinolin-8-ol,
5,5'-(naphthalen-1-ylmethylazanediyl)diquinolin-8-ol,
tert-butyl 8-hydroxyquinolin-5-yl(naphthalen-1-ylmethyl)carbamate, and
5-(((8-hydroxyquinolin-5-yl)(4-trifluoromethyl)benzyl)amino)methyl)quinolin-8-ol.

5. A composition comprising a compound according to claim 1 and a carrier.

6. A method of treating cancer or treating cancer metastasis comprising administering to an individual having cancer a compound of formula (I):

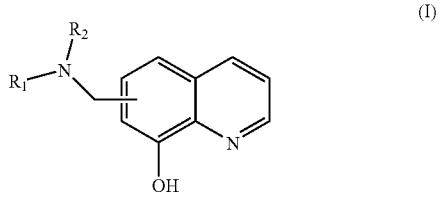

(I)

for the manufacture of a medicament intended for use as an anticancer agent, in which formula the group —CH$_2$—NR$_1$R$_2$ is in the ortho, meta or para position relative to the —OH group, and
in which
one of the radicals R$_1$ and R$_2$ represents
a hydrogen atom, a C$_1$ to C$_{10}$ alkyl group, a C$_2$ to C$_4$ alkenyl or alkynyl group or a 5-methylene-8-hydroxyquinoline group; the other represents a 5-methylene-8-hydroxyquinoline group, an aryl group, —(CH$_2$)$_n$-heteroaryl comprising one or more heteroatoms chosen from N, O and S, n being an integer between 0 and 4, a C$_4$ to C$_6$ group —(CH$_2$)$_n$-heterocycloalkyl in which the heteroatom represents N, O or S, n being an integer between 0 and 4, or alkylphenyl in which the alkyl represents C$_1$ to C$_{10}$, the phenyl group being unsubstituted or substituted with 1 or 2 halogen atoms chosen from F, Br, I and Cl or with —CF$_3$;
or one of the radicals R$_1$ and R$_2$ represents a group of formula (II) linked to the asymmetric carbon

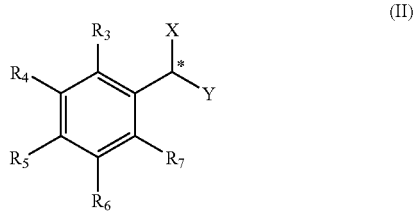

(II)

in which R$_3$, R$_4$, R$_5$, R$_6$ and R$_7$, independently of each other, represent a hydrogen atom, a C$_1$ to C$_{10}$ alkyl group, —CF$_3$, —NO$_2$, an N-5-methylene-8-hydroxyquinoline group, 1 or 2 halogen atoms chosen from F, Br, I and Cl or a group —O—R, R being a C$_1$ to C$_4$ alkyl group or —CF$_3$,
X or Y represents a hydrogen atom, a C$_1$ to C$_{10}$ alkyl group, an aryl that is unsubstituted or substituted with a C$_1$ to C$_{10}$ alkyl group, —CF$_3$ or —NO$_2$,
the other of the radicals R$_1$ and R$_2$ representing an H atom, a tert-butoxycarbonyl group (Boc), 5-methylene-8-hydroxyquinoline or —(CH$_2$)$_n$-phenyl, n being an integer between 1 and 5;
or, when one of the groups R$_1$ and R$_2$ is a group Y—N—Y' in which Y is chosen from the group formed by —(CH$_2$)$_n$—, n being an integer between 1 and 10, —(CH$_2$)$_m$-phenyl-(CH$_2$)$_p$—, the phenyl being unsubstituted or substituted with 1 or 2 halogen atoms chosen from F, Br and Cl or with a C$_1$ to C$_{10}$ alkyl group, m and p being, respectively, integers between 1 and 4, and in which Y' is 5-methylene-8-hydroxyquinoline, the other represents a hydrogen atom;
or, when one of the groups R$_1$ and R$_2$ represents a group —(CH$_2$)$_n$-naphthalene, n being an integer between 1 and 10, the naphthalene group being unsubstituted or substituted with one or more groups chosen from C$_1$ to C$_{10}$ alkyl groups, —CF$_3$ and —O—R in which R is a C$_1$ to C$_{10}$ alkyl group, the other is chosen from the group formed by a hydrogen atom, a 5-methylene-8-hydroxyquinoline group and a Boc group;
or R$_1$ and R$_2$ form a piperazine that is unsubstituted or in which at least one of the carbon atoms of the ring is substituted with a C$_1$ to C$_6$ alkyl group and in which the N atom that is not part of the group —CH$_2$—NR$_1$R$_2$ is substituted with a 5-methylene-8-hydroxyquinoline group;
or R$_1$ and R$_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —(CH$_2$)$_n$-phenyl-(CH$_2$)$_n$—Z, n being an integer between 1 and 10, in which Z represents one of the N atoms of a 1,4,8,12-tetraazacyclopentadecane or 1,4,8,11-tetraazacyclotetradecane in which the other N atoms of the ring in position 1, 4 and 8 are unsubstituted or are each independently substituted with a Boc group, and the enantiomers thereof.

7. The method according to claim 6, wherein:
one of the radicals R$_1$ and R$_2$ represents
a hydrogen atom, a C$_1$ to C$_6$ alkyl group, a C$_2$ to C$_4$ alkenyl or alkynyl group or a 5-methylene-8-hydroxyquinoline group; the other represents a 5-methylene-8-hydroxyquinoline group, an aryl group, —(CH$_2$)$_n$-heteroaryl comprising one or more heteroatoms chosen from N, O and S, n being an integer between 0 and 4, a C$_4$ to C$_6$ group —(CH$_2$)$_n$-heterocycloalkyl in which the heteroatom represents N, O or S, n being an integer between 0 and 4, or alkylphenyl in which the alkyl represents C$_1$ to C$_6$, the phenyl group being unsubstituted or substituted with 1 or 2 halogen atoms chosen from F, Br, I and Cl or with —CF$_3$;
or one of the radicals R$_1$ and R$_2$ represents a group of formula (II) linked to the asymmetric carbon

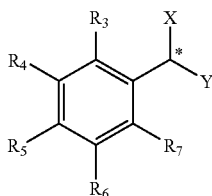
(II)

in which $R_3$, $R_4$, $R_5$, $R_6$ and $R_7$, independently of each other, represent a hydrogen atom, a $C_1$ to $C_6$ alkyl group, —$CF_3$, —$NO_2$, an N-5-methylene-8-hydroxyquinoline group, 1 or 2 halogen atoms chosen from F, Br, I and Cl or a group —O—R, R being a $C_1$ to $C_3$ alkyl group or —$CF_3$, X or Y represents a hydrogen atom, a $C_1$ to $C_6$ alkyl group, an aryl that is unsubstituted or substituted with a $C_1$ to $C_6$ alkyl group, —$CF_3$ or —$NO_2$, the other of the radicals $R_1$ and $R_2$ representing H, a Boc group, 5-methylene-8-hydroxyquinoline or —$(CH_2)_n$-phenyl, n being an integer between 1 and 5;

or, when one of the groups $R_1$ and $R_2$ is a group Y—N—Y' in which Y is chosen from the group formed by — $(CH_2)_n$—, n being an integer between 1 and 6, —$(CH_2)_m$-phenyl-$(CH_2)_p$—, the phenyl being unsubstituted or substituted with 1 or 2 halogen atoms chosen from F, Br and Cl or with a $C_1$ to $C_6$ alkyl group, m and p being, respectively, integers between 1 and 4, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 6, the naphthalene group being unsubstituted or substituted with one or more groups chosen from $C_1$ to $C_6$ alkyl groups, —$CF_3$ and —O—R in which R is a $C_1$ to $C_6$ alkyl group, the other is chosen from the group formed by a hydrogen atom, a 5-methylene-8-hydroxyquinoline group and a Boc group;

or $R_1$ and $R_2$ form a piperazine that is unsubstituted or in which at least one of the carbon atoms of the ring is substituted with a $C_1$ to $C_4$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 6, in which Z represents one of the N atoms of a 1,4,8,12-tetraazacyclopentadecane or 1,4,8, 11-tetraazacyclotetradecane in which the other N atoms of the ring in position 1, 4 and 8 are unsubstituted or are each independently substituted with a Boc group, and the enantiomers thereof.

8. The method according to claim 6, wherein:
one of the radicals $R_1$ and $R_2$ represents
a hydrogen atom, a $C_1$ to $C_4$ alkyl group, a $C_2$ to $C_4$ alkenyl or alkynyl group or a 5-methylene-8-hydroxyquinoline group; the other represents a 5-methylene-8-hydroxyquinoline group, an aryl group, —$(CH_2)_n$-heteroaryl comprising one or more heteroatoms chosen from N, O and S, n being an integer between 0 and 3, a $C_4$ to $C_6$ group —$(CH_2)_n$-heterocycloalkyl in which the heteroatom represents N, O or S, n being an integer between 0 and 3, or alkylphenyl in which the alkyl represents $C_1$ to $C_4$, the phenyl group being unsubstituted or substituted with 1 or 2 halogen atoms chosen from F and I or with —$CF_3$;

or one of the radicals $R_1$ and $R_2$ represents a group of formula (II) linked to the asymmetric carbon

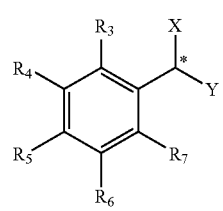
(II)

in which one of the radicals $R_3$, $R_4$, $R_5$, $R_6$ and $R_7$ represents an N-5-methylene-8-hydroxyquinoline group and the others represent a hydrogen atom, X or Y represents a hydrogen atom, a $C_1$ to $C_4$ alkyl group, an aryl that is unsubstituted or substituted with a $C_1$ to $C_4$ alkyl group, —$CF_3$ or —$NO_2$, the other of the radicals $R_1$ and $R_2$ representing H, a tert-butoxycarbonyl (Boc) group or 5-methylene-8-hydroxyquinoline;

or, when one of the groups $R_1$ and $R_2$ is a group Y—N—Y' in which Y is chosen from the group formed by — $(CH_2)_n$—, n being an integer between 1 and 4, —$(CH_2)_n$-phenyl-$(CH_2)_p$—, the phenyl being unsubstituted or substituted with 1 or 2 halogen atoms chosen from F, Br and Cl or with a $C_1$ to $C_4$ alkyl group, m and p being, respectively, integers between 1 and 3, and in which Y' is 5-methylene-8-hydroxyquinoline, the other represents a hydrogen atom;

or, when one of the groups $R_1$ and $R_2$ represents a group —$(CH_2)_n$-naphthalene, n being an integer between 1 and 4, the naphthalene group being unsubstituted or substituted with one or more groups chosen from $C_1$ to $C_4$ alkyl groups, —$CF_3$ and —O—R in which R is a $C_1$ to $C_4$ alkyl group, the other is chosen from the group formed by a hydrogen atom, a 5-methylene-8-hydroxyquinoline group and a Boc group;

or $R_1$ and $R_2$ form a piperazine that is unsubstituted or in which at least one of the carbon atoms of the ring is substituted with a $C_1$ to $C_3$ alkyl group and in which the N atom that is not part of the group —$CH_2$—$NR_1R_2$ is substituted with a 5-methylene-8-hydroxyquinoline group;

or $R_1$ and $R_2$ form a polyazamacrocycle (cyclam) representing unsubstituted 1,4,8,12-tetraazacyclopentadecane or 1,4,8,11-tetraazacyclotetradecane in which at least one of the N atoms of the ring in position 1, 4 and 8 is, independently, substituted with a Boc group, with a 5-methylene-8-hydroxyquinoline group or with —$(CH_2)_n$-phenyl-$(CH_2)_n$—Z, n being an integer between 1 and 4, in which Z represents one of the N atoms of a 1,4,8,12-tetraazacyclopentadecane or 1,4,8, 11-tetraazacyclotetradecane in which the other N atoms of the ring in position 1, 4 and 8 are unsubstituted or are each independently substituted with a Boc group, and the enantiomers thereof.

9. The method according to claim 6, wherein said compound is:
- 5-((1,4,8,12-tetraazacyclopentadecan-8-yl)methyl)quinolin-8-ol,
- tri-tert-butyl 12-((8-hydroxyquinolin-5-yl)methyl)-1,4,8,12-tetraazacyclopentadecane-1,4,8-tricarboxylate,
- tri-tert-butyl 11-((8-hydroxyquinolin-5-yl)methyl)-1,4,8,11-tetraazacyclotetradecane-1,4,8-tricarboxylate,
- 5-((1,4,8,11-tetraazacyclotetradecan-1-yl)methyl)quinolin-8-ol,
- tri-tert-butyl 11-(3-((4,11-bis(tert-butoxycarbonyl)-8-((8-hydroxyquinolin-5-yl)methyl)-1,4,8,11-tetraazacyclotetradecan-1-yl)methyl)benzyl)-1,4,8,11-tetraazacyclotetradecane-1,4,8-tricarboxylate,
- 5,5'-(propane-1,3-diylbis(azanediyl))bis(methylene)diquinolin-8-ol,
- 5-((8-(4-((1,4,8,11-tetraazacyclotetradecan-1-yl)methyl)benzyl)-1,4,8,11-tetraazacyclotetradecan-1-yl)methyl)quinolin-8-ol,
- 5,5'-(piperazine-1,4-diylbis(methylene))diquinolin-8-01,
- di-tert-butyl 4,8-bis((8-hydroxyquinolin-5-yl)methyl)-1,4,8,11-tetraazacyclotetradecane-1,11-dicarboxylate,
- 5,5'-(1,4,8,11-tetraazacyclotetradecane-1,1'-diyl)bis(methylene)diquinolin-8-ol,
- 5,5'-(1,4-phenylenebis(methylene))bis(azanediyl)bis(methylene)diquinolin-8-ol,
- 5,5'-(benzylazanediyl)bis(methylene))diquinolin-8-ol,
- 5-((benzylamino)methyl)quinolin-8-ol,
- 5-(((8-hydroxyquinolin-5-yl)(4-methylbenzyl)amino)methyl)quinolin-8-ol,
- tert-butyl 8-hydroxyquinolin-5-yl(4-methylbenzyl)carbamate,
- 5-(4-methylbenzylamino)quinolin-8-ol,
- 5-(naphthalen-1-ylmethylamino)quinolin-8-ol,
- 5,5'-(naphthalen-1-ylmethylazanediyl)diquinolin-8-ol,
- tert-butyl 8-hydroxyquinolin-5-yl(naphthalen-1-ylmethyl)carbamate, and
- 5-(((8-hydroxyquinolin-5-yl)(4-(trifluoromethyl)benzyl)amino)methyl)quinolin-8-ol.

10. The method according to claim 6, wherein said method is for the treatment of cancer metastasis and said method reduces the migration and proliferation of metastases or tumor cells.

11. The method according to claim 10, wherein the metastases or tumor cells are glioblastomas, carcinomas, sarcomas, myelomas, melanomas and mesotheliomas.

12. The method according to claim 6, wherein said cancer is oral carcinoma, bowel carcinoma, breast carcinoma, lung carcinoma, prostate carcinoma, glioblastoma, ovarian adenocarcinoma, hepatocarcinoma or lymphoblastoma.

* * * * *

UNITED STATES PATENT AND TRADEMARK OFFICE
CERTIFICATE OF CORRECTION

PATENT NO. : 8,324,243 B2
APPLICATION NO. : 12/532695
DATED : December 4, 2012
INVENTOR(S) : Jean-Louis Kraus, Olivier Blin and Frederic Champavere It is certified that error appears in the above-identified patent and that said Letters Patent is hereby corrected as shown below:

In the Specifications:

Column 4,
Lines 12-13, "5,5'-(1,4-phenylenebis(methylene)bis(azanediyl)bis(methylene) diquinolin-8-ol," should read
--5,5'-(1,4-phenylenebis(methylene))bis(azanediyl)-bis(methylene) diquinolin-8-ol,--.
Lines 16-17, "tert-butyl 8-hydroxyquinolin-5-yl(4-methylbenzyl)carbamate," should read
-- tert-butyl 8-hydroxyquinolin-5-yl(4-methylbenzyl)-carbamate,--.

Column 12,
Lines 8-9, "represents N, or S," should read --represents N, O or S,--.

Column 14,
Line 63, "in position 1, and 8" should read --in position 1, 4 and 8--.

Column 15,
Line 43, "calorimetric" should read --colorimetric--.

Column 19,
Line 53, "R$_3$, R$_4$, R5," should read --R$_3$, R$_4$, R$_5$,--.

In the Claims:

Column 24,
Lines 31-34, "di-tert-butyl 4,8-bis((8-hydroxyquinolin-5-yl)methyl)-1,4,8,11-tetraazacyclotetradecane-dicarboxylate,
5,5'-(1,4,8,11-tetraazacyclotetradecane-1,1'-diyl)bis(methylene) diquinolin-8-ol," should read
--di-tert-butyl 4,8-bis((8-hydroxyquinolin-5-yl)methyl)-1,4,8,11-tetraazacyclotetradecane-1,11-dicarboxylate,
5,5'-(1,4,8,11-tetraazacyclotetradecane-1,11-diyl)bis(methylene) diquinolin-8-ol,--.

Signed and Sealed this
First Day of October, 2013

Teresa Stanek Rea
*Deputy Director of the United States Patent and Trademark Office*

CERTIFICATE OF CORRECTION (continued)
U.S. Pat. No. 8,324,243 B2

Column 25,
Line 23, "or —($C_{1-2}$)$_n$-phenyl," should read --or —($CH_2$)$_n$-phenyl,--.
Lines 26-27, "6, —($CH_2$)$_n$-phenyl-($CH_2$)$_p$—," should read
 --6, —($CH_2$)$_m$-phenyl-($CH_2$)$_p$—,--.
Line 53, "—($CH_2$)$_n$-phenyl-($CH_2$)—Z," should read -- —($CH_2$)$_n$-phenyl-($CH_2$)$_n$—Z,--.

Column 30,
Lines 32-33, "—($CH_2$)$_n$-phenyl-($CH_2$)$_p$—" should read -- —($CH_2$)$_m$-phenyl-($CH_2$)$_p$— --.

Column 31,
Line 23, "5,5'-(1,4,8,11-tetraazacyclotetradecane-1,1'-diyl)bis(methylene)diquinolin-8-
 ol," should read
 --5,5'-(1,4,8,11-tetraazacyclotetradecane-1,11-diyl)bis(methylene)diquinolin-8-
 ol,--.